US012266430B2

(12) United States Patent
Gergely

(10) Patent No.: US 12,266,430 B2
(45) Date of Patent: Apr. 1, 2025

(54) SYSTEM, METHOD, AND APPARATUS FOR UNIVERSALLY ACCESSIBLE PERSONAL RECORDS

(71) Applicant: Robert Gergely, Los Angeles, CA (US)

(72) Inventor: Robert Gergely, Los Angeles, CA (US)

( * ) Notice: Subject to any disclaimer, the term of this patent is extended or adjusted under 35 U.S.C. 154(b) by 6 days.

(21) Appl. No.: 17/107,389

(22) Filed: Nov. 30, 2020

(65) Prior Publication Data

US 2021/0098096 A1    Apr. 1, 2021

Related U.S. Application Data

(63) Continuation-in-part of application No. 15/812,158, filed on Nov. 14, 2017, now abandoned.

(51) Int. Cl.
| | |
|---|---|
| *G16H 10/60* | (2018.01) |
| *G06F 16/182* | (2019.01) |
| *G06F 21/36* | (2013.01) |
| *G06F 21/62* | (2013.01) |
| *G06F 21/64* | (2013.01) |
| *G06K 7/14* | (2006.01) |

(52) U.S. Cl.
CPC ......... *G16H 10/60* (2018.01); *G06F 16/1837* (2019.01); *G06F 21/36* (2013.01); *G06F 21/6227* (2013.01); *G06F 21/64* (2013.01); *G06K 7/1417* (2013.01)

(58) Field of Classification Search
None
See application file for complete search history.

(56) References Cited

U.S. PATENT DOCUMENTS

| | | | |
|---|---|---|---|
| 2004/0186744 A1* | 9/2004 | Lux | G16H 40/20 705/2 |
| 2010/0042440 A1* | 2/2010 | Joao | G06Q 10/10 705/2 |

(Continued)

FOREIGN PATENT DOCUMENTS

WO    WO-2014090411 A1 *    6/2014    ............. G06F 16/22

OTHER PUBLICATIONS

"ScanMed QR Releases World's First Proactive QR Medical Alert Product." PRNewsChannel.com, Jan. 29, 2013, p. NA. ProQuest. Web. Nov. 20, 2023. (Year: 2013).*

*Primary Examiner* — Lena Najarian
(74) *Attorney, Agent, or Firm* — Omni Legal Group; Omid E. Khalifeh; Ariana K. Santoro

(57) ABSTRACT

A system, method, and apparatus for universally accessible personal records provides encrypted storage of user-specific data within a personal record linked to a personal record chain of personal records. The personal record chains are stored in immutable form across a plurality of nodes that collectively function as a dispersed, redundant personal record chain data storage system. A secure QR code may act as a patient's private key, and may be scanned by any designated third party in the world who has access to the present invention. When scanned, the private key or password may decrypt the user-specific data and provide a portion or all of the same to the designated third-party. Any changes to the user-specific data within a new personal record may be immutably recorded on the personal record chain and multiple copies and chains of personal records may be stored across more than one node.

5 Claims, 3 Drawing Sheets

(56) References Cited

U.S. PATENT DOCUMENTS

| | | | | |
|---|---|---|---|---|
| 2013/0054271 A1* | 2/2013 | Langford | ............... | G16H 10/60 |
| | | | | 705/3 |
| 2014/0316812 A1* | 10/2014 | Hathorn | ................ | G16H 40/20 |
| | | | | 705/3 |
| 2016/0300234 A1* | 10/2016 | Moss-Pultz | ............. | G06F 21/64 |
| 2017/0286717 A1* | 10/2017 | Khi | ....................... | H04W 12/08 |
| 2017/0300627 A1* | 10/2017 | Giordano | ............ | G06F 21/6245 |
| 2018/0025365 A1* | 1/2018 | Wilkinson | ......... | G06Q 30/0201 |
| | | | | 705/7.29 |

\* cited by examiner

SYSTEM, METHOD, AND APPARATUS FOR UNIVERSALLY ACCESSIBLE PERSONAL RECORDS

CROSS-REFERENCE TO RELATED APPLICATIONS

This application is a continuation-in-part of U.S. patent application Ser. No. 15/812,158 filed on Nov. 14, 2017. The content of such application is incorporated herein by reference in its entirety.

GOVERNMENT CONTRACT

Not applicable.

STATEMENT RE. FEDERALLY SPONSORED RESEARCH/DEVELOPMENT

Not applicable.

COPYRIGHT & TRADEMARK NOTICES

A portion of the disclosure of this patent document may contain material which is subject to copyright protection. This patent document may show and/or describe matter which is or may become trade dress of the owner. The copyright and trade dress owner has no objection to the facsimile reproduction by any one of the patent document or the patent disclosure, as it appears in the Patent and Trademark Office patent files or records, but otherwise reserves all copyrights and trade dress rights whatsoever.

TECHNICAL FIELD

The disclosed subject matter relates generally to personal record keeping platforms, and more particularly, to a system, method, and apparatus for universally storing and accessing personal bibliographic, government-issued, and medical records.

BACKGROUND

For years, politicians and medical professionals have recognized the need to computerize health records so as to avoid dangerous medical mistakes, reduce costs, and improve health care. In fact, in 2004, U.S. politicians called for a modernization of American health care wherein within ten years every patient should have an electronic medical record (EMR) or electronic health record (EHR).

Unfortunately, over ten years later few patients have seen these promises come to pass. Intransigent issues such as interoperability and cost of implementation have prevented high-quality EMR architecture from taking hold and bringing about the benefits many see as possible.

Many presently-available poor substitutes for this vision, faulty EMR products and systems, force physicians to spend two hours performing "administrative" tasks for every hour spent providing patient care. This frustrating situation has resulted, unsurprisingly, in epidemic physician burnout and an unwillingness to adopt EMR systems.

Furthermore, not only are presently-available EMR products and systems cumbersome and unmanageable, they are also egregiously expensive for both medical professionals and insurance companies. The cost to medical institutions to implement, maintain, upgrade, and monitor these systems is not unjustifiably high and on the rise. And, some experts estimate that mistakes within these EMR systems cost insurance companies billions annually in double testing, file storage, and mismatched medical records.

Difficulties also arise with respect to personal acquisition and storage of more generalized personal records, such as government issued identifications, and privately and publicly issued and maintained ownership records, financial records, educational records and others.

What is needed therefore is an alternate record architecture: a QR-code enabled universal ID attached to an electronic personal file, backed up using secure techniques, that the patient populates and controls. Such a solution could also serve as an individual's social security number. This "Personal Record" (PR) could be assigned at birth or anytime during a person's life, and provide a longitudinal unified personal record used to glean genetic and genomic information. And, because such a system would be designed to run on any computer platform, it could solve EMR's interoperational problems. In so doing, the system would reduce the physician's administrative burdens, benefitting both physicians—or other designated third parties, such as government recordkeepers, among others—and patients. Such a system would also save insurance companies great sums of money. Yet, such a system's cost would be negligible compared to current solutions.

Attempts to meet these needs have been made with varying degrees of effectiveness. For example, and with reference to the field of healthcare for brevity and the sake of example only, U.S. Patent Application Publication No. 2015/0332283, incorporated by reference herein it its entirety, discloses a healthcare transaction verification system and method that utilizes blockchain databases. While systems that utilize blockchain technology offer unparalleled data security, this disclosure fails to provide a scannable barcode option or other quick-access portal to utilize the protected information.

Another attempt can be seen in the disclosure of U.S. Patent Application Publication No. 2017/0149560, incorporated by reference in its entirety herein, which generally discloses an electronic records system and method that utilizes blockchain technology and that provides for matrix barcode authentication login. Yet, this disclosure falls short as well. By not sufficiently providing for an adequate translation mechanism, such a disclosure could be of little use in a foreign country.

Another example is U.S. Patent Application Publication No. 2017/0039330, incorporated by reference in its entirety herein, which generally discloses another blockchain-based electronic medical records system and method. Similar to the above, this disclosure fails to provide quick and secure access to the patient's electronic medical records through a scannable barcode portal.

As can be seen, a need exists for a system, method, and apparatus for universally accessible personal medical records, and even personal bibliographic records more broadly, collected and immutably authenticated from the birth of the user, which are linked to matrix barcodes as private keys; remain under the ownership, control, and possession of the user; and provide universal, secure access to the user-specific data from anywhere in the world.

SUMMARY

The present disclosure is directed to a system, method, and apparatus for universally accessible personal records that, in some embodiments, provides for secure, territory-independent, provider-independent access to user-specific data, such as but not limited to, medical records and bibliographic records such as those identifying records issued by certain governmental bodies. It is an object of the present invention to meet the need for a QR-code enabled universal ID attached to a comprehensive electronic file that is backed up using secure techniques, that an individual populates and controls as to his or her own medical and personal bibliographic information, and which may be verified by a third party designated by the type of personal information defining the update. In an embodiment, it is contemplated that this system, method and apparatus result in continuity of care and longitudinal record accuracy for medical and personal bibliographic records. Indeed, owing to the accuracy and verification provided for, the personal record may, in some embodiments, serve as an individual's social security number.

The Personal Record ("PR") of the present invention may comprise, in some embodiments, a cradle-to-grave secure "vault" in the cloud individually connected to the owner/user to which the user or another authorized user (such as a parent or guardian) may have instant access, and that the user/authorized user may populate with the user's medical records, personal bibliographic information, or other pertinent information. In some embodiments, the PR may be provided to every baby born, or may be assigned to an individual at any time in the person's life or after their death. In some embodiments, the PR may be assigned to civilians, members of the armed forces, public servants working for the government (e.g. The Department of Defense), or veterans (such as at the Department of Veterans Affairs or "VA").

In some embodiments, access to the PR may be by a matching specific QR Code. The QR code may be available on a mobile phone and a backup printed on a plastic card-MedicalPassport (size of a credit card). The QR code may also serve as a universal ID. Since smartphones can scan the QR code globally, the present invention may be available anywhere in the world, in any language, and at any time, thus potentially providing accurate medical and other personal history anywhere in the world anytime and in any language.

The present invention, in some embodiments, may comprise a decentralized electronic database distributed across various computers, or "nodes." The decentralized database may securely store and transmit personal records ("PRs") between computers, other electronic devices, or nodes. The present invention may use data matrix codes (or quick response "QR" codes) as private keys that "unlock" or decrypt a PR when a user scans the QR code.

In some embodiments, a node may be any suitable electronic device, such as but not limited to a server, a mobile device, or desktop computer, that is linked to one or more networks provided by the present invention and that can perform the functions of the present invention, such as storing, linking (or "chaining"), encrypting, decrypting, and transmitting PRs. Each node may be configured to independently and automatically verify, update, link, and store each personal record in the personal record chain ("PR chain").

Generally, a PR may comprise, at least, storage information and user-specific data. In some embodiments, user-specific data may resemble an electronic dossier that the patient can manage and control. The PR may contain a complete copy of the patient's electronic medical record, including but not limited to medical history, charts, labs, imagery, healthcare provider notes and diagnosis. A PR may also contain anything the patient deems pertinent to the patient's medical care, such as but not limited to online articles or the patient's own notes on how certain medications made the patient feel, and so forth. Storage information may comprise details about the PR, such as its date and time of creation, its link to a previous PR, and instructions for the next PR's connection to the present PR. In some embodiments, one or more elements of storage information may be recorded as a cryptographic hash.

Each PR may be an immutable record stored in a duplicate copy across all nodes. Instead of known solutions that place the patient's file in medical personnel hands, the present invention may allow the patient to control when a new PR is created. In other embodiments, the present invention may provide that a new PR may be automatically created whenever the PR is accessed or changed. In both scenarios, the new, updated PR may be linked to the patient's previous PR in the decentralized electronic database and stored on all the nodes as part of the patient's PR chain.

In some embodiments, the QR code of the present invention may unlock 1) the private key or password for a PR, 2) an individual's social security number, and 3) Universal Identification Number ("Universal ID" or even "User ID" as the case may be). Additionally, in some embodiments, the QR code may itself be or substitute for an individual's social security number. Such functionality is contemplated to provide more security against identify theft than known solutions. In some embodiments, a user may download one copy of the QR code and use a single application to display the QR code on a device's screen. Using the device's settings, the user may select whether, when the QR code is scanned, the device displays, unlocks, and/or transmits the user's social security number, their Universal ID, and/or PR. In some embodiments, the present invention may store an identical QR code in more than one location on the device and use more than one application to display the QR code on the device's screen, so that each application utilizes the QR code for only one of the user's social security number, their Universal ID, or PR. Thus, in such an embodiment, the user controls the QR code's function by selecting an application, rather than by relying on a settings choice. For purposes of the present disclosure, unless otherwise indicated, the QR code is presumed to be used with respect to the PR function.

In some embodiments, a person may be assigned a QR code and associated social security number, PR, and Universal ID at birth. In some embodiments, a person may be assigned a QR code and associated social security number, PR, and Universal ID at any time during the user's life or even after the user's death.

It is contemplated that a user may own, manage, and control their own PR. Generally, an authorized user (the user or the user's guardian, if the user is a minor) may control and manage the user's PR. Since the Universal ID may be assigned at birth, this renders any need for a user to "request" their personal records—such as government issued records and personally or professionally generated medical records—obsolete. Indeed, rather than requesting access to any of the following, for example only and not limitation: a medical provider's record of themselves; a financial institution's record of a user's accounts; local or federal government's record of a user's taxes and properties; public and/or private institution's or even employer's records of a user's certificates, licenses, diplomas and other records; the user is effectively empowered to grant others access to their own records at any place as needed or desired. It is more generally contemplated, then, that the user, who may from time to time be a patient undergoing medical services, is empowered to personally input their own notes, official records, and even other information such as ancestral data, letters, diary entries, and more, at their own discretion.

In the event that a user uploads, creates, or generates data on their own PR, it is contemplated that a designated third party may be recruited or assigned to verify or authenticate such data. The designated third party may be selected or assigned based on the nature of the particular data defining the PR. For instance, a user's physician may be a designated third party recruited or assigned to verify data associated with the physician's care or treatment of the user. An authorized individual within a state's department of motor vehicles may be a designated third party selected or assigned to verify a user's driver's license and/or vehicle registration data. An authorized individual at a school may be a designated third party may be selected or assigned to verify a user's transcripts and other education records received therefrom, etc. Of course, these are offered by way of limited example for the sake of brevity. One skilled in the art will recognize that a number of private and public actors and/or institutions may be designated third party to verify data comprising various data comprising the PR.

Although the invention enables a user's addition to their PR without the aid, input, or facilitation of a medical provider or other designated third party, it is contemplated that providing means for verifying such data by way of such designated third party, who may in the exemplary case be a user's treating physician, ensures the continued accuracy of the data over the life time of the user.

In some embodiments, however, a designated third party—such as a medical professional, governmental body, or public or private institution—may directly upload or record data to the user's PR. Such data may include, for instance, a user's birth certificate, social security number, passport, medical history, record of care, banking information, ancestral data, property ownership records, tax record, and more. In such instances, a user may verify that data linked to the PR chain by the designated third party is accurate. It should be recognized that owing to decentralized storage over a plurality of nodes, each PR is highly protected from manipulation, and thus each instance of verification either by the user or a designated third party, may be immutably recorded on the PR chain.

In other words, it is contemplated that the source of user data as well as the fact and source of verification of user data is recorded each time the record is accessed. That is, information placed in the record may be readily traced since entries are "hashed" (discussed in further detail below). Should any question of the authenticity or accuracy of the user's data arise, the chain may be examined, and the source of any aberrations easily identified. This infallibly authenticates the user's lifetime of innumerable personal records.

Although it is contemplated that the personal record may comprise government-issued bibliographic information, it will also be recognized that because of the means for authenticating the PR disclosed above and the fact that the personal record is also owned by the user throughout their life, the identity of the owner of the record can be readily verified using the personal record itself, whether or not such data as a user's birth certificate and other government-issued bibliographic data is stored therein. The longitudinal nature of the personal record makes it a reliable method of identifying each individual user, rendering it a reasonable alternative to other means of providing identification, such as the social security number and even passport. It should be apparent, then, that this structure of longitudinal records for every citizen user will completely solve the interoperability dilemma currently being faced by medical systems around the world.

Furthermore, in some embodiments, both the user and designated third party, such as the medical professional or authorized member of another designated institution may upload, create, and manage the patient's PR. And in still other embodiments, a user may determine if, how, and when a designated third party or institution may upload, create, and manage the patient's PR, such as for example by turning access to a designated third party on or off. Examples of instances where a person or entity other than the user may control or manage the PR might include scenarios wherein the patient has diminished cognition or has lost capacity.

For the sake of brevity, the following exemplary discussion is directed to PRs as medical records in particular. It will be recognized that this will apply more broadly, though, to all user data and records which may form a part of the PR in lieu of or in addition to the medical records.

One exemplary sequence involving a PR might begin with a user's, or more specifically, a patient's doctor visit, wherein the patient might be sent for tests, laboratory or imaging. When the results come back to the doctor, the doctor may, and in some embodiments must, send the patients the results along with the doctor's diagnosis and accompanying instructions via e-mail. When the patient receives the information, the present invention may also provide an opportunity to learn about the diagnosis via links to internet information. In some embodiments, the patient may be able to simply forward the email and/or the information to the patient's PR. Because, in some embodiments, the PR may be populated by the patients themselves, the present invention may provide for or otherwise cause the patients' involvement in their care to be maximal. And, due to its backend blockchain technology, the PR may also become a medico-legal record and may prevent a patient from going back and altering the PR.

In some embodiments, another or alternative sequence of PR creation and utilization may be a more automated embodiment. For example, and not by way of limitation, first, an element of user-specific data such as for example part or all of an electronic medical record, an x-ray or other diagnostic, may be obtained by a medical professional or medical institution. Then, the present invention may then provide that the patient specific data is automatically included in the patient's PR, and in some embodiments, the system may then create a new PR linked to the old PR that includes the new or updated data. The patient or authorized user may then share the data and/or the new or updated PR with a medical professional. Or, in some embodiments, the present invention may provide the data and/or the updated PR directly to the medical professional. The patient may then be seen by the medical professional, which may result in new or updated data, which may be sent to the patient and may be included in the PR, which in some embodiments may result in a new PR reflecting the updated or new information that is linked to the previous PR. The updated PR, in some embodiments the newest copy of the PR, may then be used in the next patient care situation.

In some embodiments, the data may be shared simultaneously with the medical professional and the patient or authorized user. In some embodiments, the data may be shared with only the medical professional. In some embodiments, the data may be shared with the medical professional and then the patient or authorized user, or vice versa.

In some embodiments, the present invention may provide the data to a patient by email, a webpage, or another interface, and in some embodiments, the data may be automatically added to the existing data within the PR. If a PR does not exist for the patient, the present invention may provide that the patient may create a PR or direct that a PR be formed. The PR may then be updated and managed as described herein, and may provide an updated, secure reference for the patient's point of care treatment and analysis.

In some embodiments, the PR's storage information may be publicly available, semi-publicly available, or viewable only by permission. Similarly, the user-specific data may be publicly available, semi-publicly available, or viewable only by permission. More specifically, in some embodiments, the user-specific data may be entirely public and visible as a read-only copy to anyone who can access the network. In some embodiments, the user-specific data may be visible as a read-only copy but de-identified. In some embodiments, the user-specific data may be unavailable for view unless the viewing person or machine utilizes a patient's private key.

The QR code (or Universal ID at times herein) may serve as a private key, in some embodiments, as that term is generally used in public key cryptography. In some exemplary and non-limiting embodiments, when a healthcare provider or other designated third party using the present invention scans a user's—or in the exemplary case, a patient's—QR code, the designated third party may access the user/patient's PR. In some embodiments, only one QR code may be used at a time, and in some embodiments, only by the user/patient. In some embodiments, the patient's QR code may be used by more than one person or entity at a time. It is contemplated that the patient may be able to set preferences within the present invention, or utilize a secondary document such as a wallet card, in some embodiments referred to as a "medical passport" or "medicalpassport," to determine who or what may utilize the patient's QR code, in what manner, and to what extent.

The present invention may provide that when a new PR is created, it may link to the patient's previous PR in the manner known in the block chain database art, by using the storage information within the PR. By creating a linked series of immutable PRs, the present invention may provide a secure chain of medical history information. As discussed more fully herein, the chain information may comprise one or more cryptographic hashes. For example, if the second PR contains the first PR's hash, the link between the two may be verified. By creating a new hash for each PR, and including that hash in the second PR, the present invention may provide for a traceable chain of PRs.

The personal record chain database of the present invention may utilize various cooperative or decentralized computing principles. In some embodiments, the personal record chain database of the present invention may utilize principles or techniques drawn from cloud computing, thin-cloud computing, fog computing, or even "blockcloud" computing. The present invention may provide that the software, systems, methods, applications, computer programs, and so forth required to execute one or more instructions, methods, computer programs, or functions of the present invention may be stored on nodes, a cloud, thin cloud, fog, or blockcloud server structure. By way of illustration and not limitation, a cloud-based program or application may be downloaded by a user that may incorporate a matrix barcode scanner and data display capabilities, such as the ability to display patient charts, photographs, x-rays and other scans, and any other element of user-specific data.

The present invention may also provide for one or more interface elements, such as by way of illustration and not limitation, a desktop software program, a mobile application, or a website, that enables the user, a healthcare provider, a family member, or other member of the public to view one or more elements of a PR. By way of illustration and not limitation, a website may host an interface, wherein a login action could take a user to an individual's webpage. On the webpage, the present invention may describe or link to one or more elements of the individual's PR. By way of illustration and not limitation, such a page may contain a randomized identifier, the present PR's hash, a link to the PR's previous hash, and one or more links to one or more elements of user-specific data. In some embodiments, when viewed by a member of the general public, the webpage and the PR information may be hidden, randomized, or otherwise unreadable. Or in some embodiments, when viewed by a member of the general public, the webpage and the PR information may be deidentified but otherwise viewable. In some embodiments, when "unlocked" via the QR code, the PR may display unencrypted versions of the user-specific data, along with the hashes.

The present invention may comprise some elements of traditional block chain database encryption, storage, management, and access. The present invention may also make use of other, more widely-used technologies, such as cloud computing, emails, and text messages. The present invention may also draw upon, digitize, or otherwise incorporate paper documents in some embodiments.

One or more of the above-disclosed embodiments, in addition to certain alternatives, are provided in further detail below with reference to the attached figures. The disclosed subject matter is not, however, limited to any particular embodiment disclosed.

Figure 1:
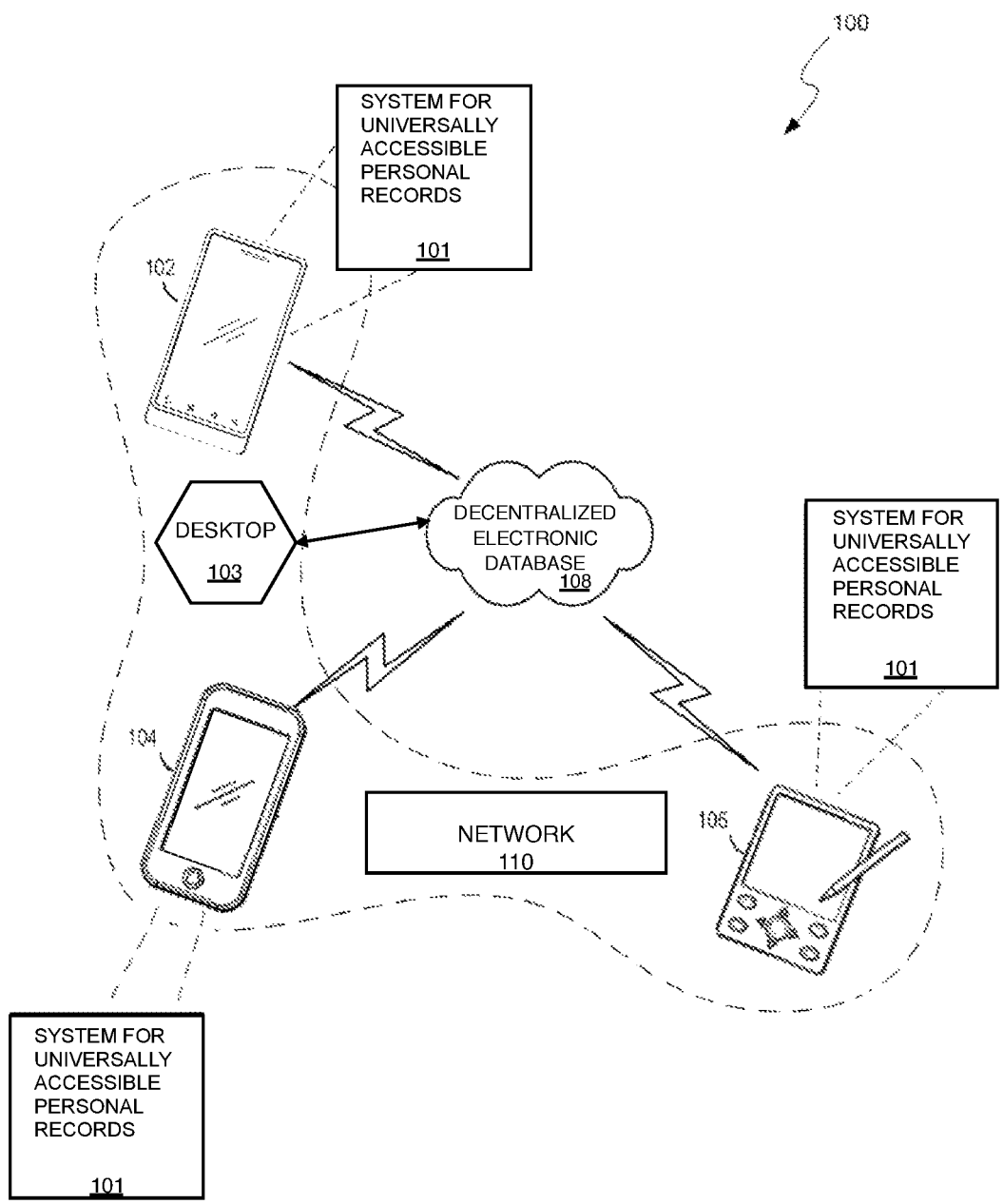
FIG. 1 is a block diagram of a networked environment in which an exemplary embodiment of a system for universally accessible personal records is implemented.

One embodiment of the invention is implemented as a program product for use with a computer system. The program(s) of the program product defines functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive) on which information is permanently stored; (ii) writable storage media (e.g., floppy disks within a diskette drive or hard-disk drive) on which alterable information is stored. Such computer-readable storage media, when carrying computer-readable instructions that direct the functions of the present invention, are embodiments of the present invention. Other media include communications media through which information is conveyed to a computer, such as through a computer or telephone network, including wireless communications networks. The latter embodiment specifically includes transmitting information to/from the Internet and other networks. Such communications media, when carrying computer-readable instructions that direct the functions of the present invention, are embodiments of the present invention. Broadly, computer-readable storage media and communications media may be referred to herein as computer-readable media.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-readable format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "couple," "coupled," "couples," "coupling," and the like should be broadly understood and refer to connecting two or more elements or signals, electrically, mechanically or otherwise. Two or more electrical elements may be electrically coupled, but not mechanically or otherwise coupled; two or more mechanical elements may be mechanically coupled, but not electrically or otherwise coupled; two or more electrical elements may be mechanically coupled, but not electrically or otherwise coupled. Coupling (whether mechanical, electrical, or otherwise) may be for any length of time, e.g., permanent or semi-permanent or only for an instant.

DETAILED DESCRIPTION

Having summarized various aspects of the present disclosure, reference will now be made in detail to that which is illustrated in the drawings. While the disclosure will be described in connection with these drawings, there is no intent to limit it to the embodiment or embodiments disclosed herein. Rather, the intent is to cover all alternatives, modifications and equivalents included within the spirit and scope of the disclosure as defined by the appended claims.

Because each PR is an immutable copy stored in redundant form across the present invention's decentralized electronic database, neither the user/owner of the PR nor anyone else may easily alter the PR's contents, including specific electronic records/data within the PR. As such, the present invention provides for a reliable, secure, user-controlled, user-managed electronic record and dossier that an authorized user may share as directed or permitted by the user simply by allowing the authorized user(s) to scan the user's QR code. The present invention also, in some embodiments, provides for the authorized user to be the caretaker of the PR's contents, which enables universal access unrestricted by differences in electronic records software programs.

The following detailed discussion is directed to personal records which may be personal medical records for the sake of brevity. It will be recognized that the discussion and invention is applicable more broadly to a wide variety of personal records such as, but not limited to, educational records, employment records, financial records, ancestral records, government issued records, personal journals and diaries, among innumerable others. As such, one skilled in the art will recognize that the invention is not limited to medical records.

In an embodiment, the system, method, and apparatus are directed to a user's personal records—or PRs—as including such user's medical history. The generation of such PR may begin at the user's—hereinafter a "patient's"—first medical visit, which could be while the patient was an infant. The present invention may provide that the patient's parents may monitor and control the PR until the patient is eighteen years of age. At a typical medical visit, the present invention may provide that a medical professional may scan the patient's QR code and the patient may then share the PR's contents with the medical professional(s). With each medical visit, the present invention may provide that the person in charge of the patient's PR (either the patient or the patient's parents, if the patient is under eighteen years of age, collectively, the "authorized user") may receive an updated electronic medical record from the medical provider, whereupon the authorized user may upload the updated electronic medical record into the PR. At the next medical visit, or at any time the authorized user may choose, the authorized user may allow the next medical professional to access the PR by allowing the medical professional to scan the patient's QR code and access the PR's contents. The doctor may then update the electronic medical record, or provide other content, and the present invention may provide that the authorized user may receive the updated electronic medical record and other information, if applicable. As before, the authorized user may include the new information, including the updated electronic medical record, into the PR. The next time the patient goes for another medical visit, the authorized user may allow the medical professional(s) access again, new patient or user-specific information may be created and shared with the authorized user or third party, and the authorized user may cause a new PR to be created as described elsewhere herein.

The present invention contemplates, in some embodiments, storage of user-specific data, including but not limited to medical records, in a block chain-like system wherein a series of immutable records are stored across a variety of nodes that act as a cloud-like storage system. In some embodiments, the present invention may differ from some, but not all, block chain programs in that some embodiments may provide that the user-specific medical data may be encrypted and may not be viewed by the public, the nodes, or persons with access to the nodes. In some embodiments, some but not all of the user-specific data may be encrypted and subject to the viewing restrictions detailed herein. In some embodiments, the present invention may provide that a secure QR code may act as a patient's private key or password, and may be scanned by any medical professional in the world who has access to the present invention. When properly scanned, the present invention may provide some or all of the encrypted information to the medical professional from the authorized personal medical record, which may be the most recent personal medical record, the most recent personal medical record on the longest chain, or other personal medical record having the indicia of paramount reliability within the system and method. Once accessed, the present invention may provide that the medical professional or other person or entity having accessed the user-specific data may be enabled to make one or more changes to the data, such as an update to the patient's record.

The present invention may comprise a system for, in part, universally accessible personal medical records, among other types of personal records. More specifically, in some embodiments, the present invention may provide for a non-transitory, tangible computer-readable medium having stored thereon computer-executable instructions, which, when executed by a computer processor, enable one or more computers coupled to a network to execute a system for universally accessible personal records, the method comprising configuring, by a computing system, at least one personal record chain-configured data bank distributed across a plurality of computer networking systems, wherein the plurality of computer networking systems comprises at least one node; receiving, by the computing system, at least one item of user-specific data specific to the user/owner of the personal record, such as a patient, wherein the at least one item of user-specific data pertains to the user; encrypting, by the computing system, the at least one item of user-specific data into at least one item of encrypted user-specific data; creating, by the computing system, a first personal record, comprising: (a) a first personal record hash at least comprising the first personal record's time and date of creation, (b) the at least one first item of encrypted user-specific identification, and (c) at least one computer system-implementable instruction for linking a second personal record to the first personal record; storing, by the computing system, the first personal record on at least one node.

The method may further comprise the steps of generating, by the computing system, at least one matrix barcode, wherein the at least one matrix barcode is unique; assigning, by the computing system, one matrix barcode to one encrypted personal record, wherein the matrix barcode operates as a private key; assigning, by the computing system, the matrix barcode to a first electronic device associated with the patient; scanning, by at least one second electronic device, the matrix barcode; generating, by the at least one second electronic device, an authorization request; sending, by the at least one second electronic device, the authorization request to the computing system; converting, by the computing system, the authorization request to an activation of the private key; decrypting, by the computing system, the at least one item of first encrypted user-specific identification within the first personal record into at least one unencrypted item of user-specific data; transmitting, by the computing system, at least one unencrypted item of user-specific data to the at least one second electronic device.

The method may further comprise the steps of accessing, by the at least one second electronic device, the at least one unencrypted item of user-specific data; generating, by the at least one second electronic device, an update to the at least one unencrypted item of user-specific data, wherein the update comprises a change to the unencrypted user-specific data; sending, by the at least one second electronic device, the update to the computing system; receiving, by the computing system, the update; solving, by at least one node, the at least one computer system-implementable instruction for linking a second personal record to the first personal record as at least one solution; securely sharing, by the at least one node, the solution with at least one other node; combining, by the computing system, the update with the unencrypted user-specific data into at least one item of unencrypted updated user-specific data; encrypting, by the computing system, the at least one item of unencrypted updated user-specific data into at least one item of encrypted updated user-specific data.

The method may further comprise the steps of creating, by the computing system, a second personal record, comprising: (a) second personal record hash indicating, at least, the second personal record's time and date of creation, (b) the first personal record hash, (c) at least one item of encrypted updated user-specific identification, and (d) at least one computer system-implementable instruction for linking another personal record to the current personal record; and storing, by the computing system, the second personal record on at least one node.

With continued respect to the method, in some embodiments the at least one unencrypted item of user-specific data may only be accessed by one second electronic device at a time. In some embodiments, the at least one unencrypted item of user-specific data may be accessed by more than one at least one second electronic device at a time.

With continued respect to the method, in at least one embodiment, the at least one second electronic device may be configured to translate the at least one unencrypted item of user-specific data into a specified language at the time of access. In some embodiments, (a) the authorization request may contain a language translation specification; (b) the computing system may be configured to decrypt the at least one item of first encrypted user-specific identification within the first personal record into at least one unencrypted item of translated user-specific data, wherein the at least one unencrypted item of translated user-specific data conforms to the language translation specification; (c) the computing system may be configured to transmit the at least one unencrypted item of translated user-specific data to the at least one second electronic device; and (d) the at least one second electronic device may be configured to access the at least one unencrypted item of translated user-specific data.

With continued respect to the method, in at least one embodiment, the update may record access to, but not alterations of, to the at least one unencrypted item of user-specific data. In some embodiments, the update may record access and alterations to the at least one unencrypted item of user-specific data.

With continued respect to the method, in at least one embodiment, the at least one item of encrypted updated user-specific data, when viewed by a node, may be presented as deidentified user-specific data. In some embodiments, the at least one item of encrypted updated user-specific data, when viewed by a node, may be presented as anonymous user-specific data.

The present invention may comprise a system for universally accessible personal records. In some embodiments, the system may comprise at least one computing system distributed across a plurality of computer networking systems, wherein the plurality of computer networking systems comprises at least one node, wherein the at least one computing system is configured to (a) receive at least one item of user-specific data, wherein the at least one item of user-specific data pertains to a patient; (b) encrypt the at least one item of user-specific data into at least one item of encrypted user-specific data; (c) create a first personal record, comprising: (i) a first personal record hash comprising at least the first personal record's time and date of creation, (ii) the at least one first item of encrypted user-specific identification, and (iii) at least one computer system-implementable instruction for linking a second personal record to the first personal record; (d) store the first personal record on at least one node; (e) generate at least one matrix barcode, wherein the at least one matrix barcode is unique; (f) assign one matrix barcode to one encrypted personal record, wherein the matrix barcode operates as a private key; (g) assign the matrix barcode to a first electronic device associated with the patient; (h) receive an authorization request from at least one second electronic device; (I) convert the authorization request to an activation of the private key; (j) decrypt the at least one item of first encrypted user-specific identification within the first personal record into at least one unencrypted item of user-specific data; (k) transmit the at least one unencrypted item of user-specific data to the at least one second electronic device; (l) receive an update from the at least one second electronic device; (m) solve the at least one computer system-implementable instruction for linking a second personal record to the first personal record as at least one solution; (n) securely share the solution with at least one node of the computer networking system; (o) combine the update with the unencrypted user-specific data into at least one item of unencrypted updated user-specific data; (p) encrypt the at least one item of unencrypted updated user-specific data into at least one item of encrypted updated user-specific data; (q) create a second personal record, comprising (i) a second personal record hash comprising at least the second personal record's time and date of creation, (ii) the first personal record hash, (iii) at least one item of encrypted updated user-specific identification, and (iv) at least one computer system-implementable instruction for linking another personal record to the current personal record; and (r) store, by the computing system, the second personal record on at least one node In some embodiments, the system may provide that the first electronic device may be configured to, at least, (a) receive and store the matrix barcode; (b) associate the matrix barcode with the patient; and (c) display the matrix barcode on a screen;

In some embodiments, the system may provide that the at least one second electronic device may be configured to: (a) scan the matrix barcode from the screen; (b) generate the authorization request; (c) send the authorization request to the computing system; (d) access the at least one unencrypted item of user-specific data; (e) generate the update to the at least one unencrypted item of user-specific data, wherein the update comprises a change to the unencrypted user-specific data; and (f) send the update to the computing system.

With continued respect to the system, in some embodiments the at least one unencrypted item of user-specific data may only be accessed by one electronic device at a time. In some embodiments, the at least one unencrypted item of user-specific data may be accessed by more than one electronic device at a time.

With continued respect to the system, in some embodiments the at least one second electronic device may be configured to translate the at least one unencrypted item of user-specific data into a specified language at the time of access. In some embodiments (a) the authorization request may contain a language translation specification, (b) the at least one computing system may be configured to decrypt the at least one item of first encrypted user-specific identification within the first personal record into at least one unencrypted item of translated user-specific data, wherein the at least one unencrypted item of translated user-specific data conforms to the language translation specification, (c) the at least one computing system may be configured to transmit the at least one unencrypted item of translated user-specific data to the at least one second electronic device; and (d) the at least one second electronic device may be configured to access the at least one unencrypted item of translated user-specific data.

With continued respect to the system, in some embodiments the update may record access to, but not alterations of, to the at least one unencrypted item of user-specific data. In some embodiments, the update may record access and alterations to the at least one unencrypted item of user-specific data.

With continued respect to the system, in some embodiments the at least one item of encrypted updated user-specific data, when viewed by a node, may be presented as deidentified user-specific data. In some embodiments, the at least one item of encrypted updated user-specific data, when viewed by a node, may be presented as anonymous user-specific data.

The present invention may comprise an apparatus for universally accessible personal records. In some embodiments, the apparatus may comprise at least one computing system distributed across a decentralized electronic database, wherein the decentralized electronic database comprises at least one node, and wherein the at least one computing system is configured to: a) receive at least one item of user-specific data, wherein the at least one item of user-specific data pertains to a patient; b) encrypt the at least one item of user-specific data into at least one item of encrypted user-specific data; c) create a first personal record, comprising i) at least one first storage instruction, wherein the at least one first storage instruction contains creation information for the first personal record and instructions for linking a second personal record to the first personal record; and ii) the at least one first item of encrypted user-specific identification; d) store the first personal record on at least one node; e) generate at least one matrix barcode, wherein the at least one matrix barcode is unique; f) assign one matrix barcode to one encrypted personal record, wherein the matrix barcode operates as a private key; g) assign the matrix barcode to a first electronic device associated with the patient; h) receive an authorization request from at least one second electronic device; i) convert the authorization request to an activation of the private key; j) decrypt the at least one item of first encrypted user-specific identification within the first personal record into at least one unencrypted item of user-specific data; k) transmit the at least one unencrypted item of user-specific data to the at least one second electronic device; l) receive an update from the at least one second electronic device; m) combine the update with the unencrypted user-specific data into at least one item of unencrypted updated user-specific data; n) encrypt the at least one item of unencrypted updated user-specific data into at least one item of encrypted updated user-specific data; o) create a second personal record, comprising: i) the at least one item of encrypted updated user-specific identification; ii) the creation information for the first personal record; and iii) at least one second storage instruction, wherein the at least one second storage instruction contains creation information for the second personal record and instructions for linking a third personal record to the second personal record; p) store the second personal record on at least one node; and q) share the second personal record on at least one other node.

With continued respect to the apparatus, the first electronic device may be configured to: a) receive and store the matrix barcode; b) associate the matrix barcode with the patient; and c) display the matrix barcode on a screen.

With continued respect to the apparatus, the at least one second electronic device may be configured to: a) scan the matrix barcode from the screen; b) generate the authorization request; c) send the authorization request to the computing system; d) access the at least one unencrypted item of user-specific data; e) generate the update to the at least one unencrypted item of user-specific data, wherein the update comprises a change to the unencrypted patient specific data; and f) send the update to the computing system.

FIG. 1 illustrates an exemplary embodiment of the present invention which includes a plurality of electronic devices communicatively coupled to one another. By way of example, and not limitation, FIG. 1 illustrates mobile devices 102, 104, and 106, and desktop computer 103 that incorporate a system for universally accessible personal records 101 and are communicatively coupled via a personal record chain-configured database 108. Each of the mobile devices may be embodied as a mobile computing device such as, for example and without limitation, a smartphone or tablet computer that incorporates cellular telephone functionality. Notably, the communications network can use one or more of various communications types such as, for example and without limitation, cellular and Wi-Fi communications. In some embodiments, one or more nodes (not pictured) may take the place of one or more of mobile devices 102, 104, and 106, and desktop computer 103.

Users of desktop computer 103 and mobile devices 102, 104, and 106 may be users of at least one network 110 known to those skilled in the art. For instance, as noted above, network 110 may comprise a peer-to-peer network, a cloud-based computing network, a fog computing network, a blockcloud computing network, or any other network 110 known in the art capable of secure data transfer. In some embodiments, network 110 may be facilitated by a website that may require a registration and login prior to use.

In one embodiment, a PR may be stored in multiple copies across personal record chain-configured database 108 on one or more nodes (not pictured). In some embodiments, each node may contain and run the software, hardware, firmware, or any other component necessary, to run the present invention. More specifically, each node may provide for a computer system that can run the program of the present invention, create, store, and link (or "chain") PRs to other PRs. Each node may also provide for computational power sufficient to perform hash functions, other one-way encryption functions, two-way encryption functions, public key encryption functions and programs, symmetric encryption and symmetric key encryption functions and programs, along with any other function that may be used or provided for by the present invention.

In brief, the original or "genesis" PR may comprise, at least, a hash that records a timestamp representing the PR's creation date and time (along with, in some embodiments, other information), encrypted user-specific data, and instructions for the linking of the second PR to the present PR. In some embodiments, the instructions may comprise a mathematical problem to be solved. In some embodiments, system for universally accessible personal records 101 may provide that the solution is provided to one or more nodes in personal record chain-configured database 108. In some embodiments, some or all of the nodes in personal record chain-configured database 108 may be equally able to solve the instructions, and therefore some or all of the nodes may discover the solution at roughly the same time, thus ensuring uniformity of record-keeping across personal record chain-configured database 108. Additional PRs may be linked to the genesis personal record, and may comprise a new timestamp hash unique to that personal record, the previous personal record's hash, encrypted updated user-specific data, and instructions for the next personal record as detailed above.

As described elsewhere in more detail herein, personal record chain-configured database 108 may be configured to associate a PR, and the user-specific data within the PR, with a QR code. In some embodiments, the QR code may be stored on any or several of desktop computer 103 and mobile devices 102, 104, and 106. In some embodiments, the QR code may be displayed on at least one of desktop computer 103 and mobile devices 102, 104, and 106. The QR code thus displayed may be scanned by at least one of desktop computer 103 and mobile devices 102, 104, and 106, or by a different scanning device such as a hand-held scanner configured to work with the present invention (not pictured).

In some embodiments, the present invention may provide that one or more of desktop computer 103 and mobile devices 102, 104, and 106 may serve as a first electronic device. In such a configuration, one or more of desktop computer 103 and/or mobile devices 102, 104, and 106 may be configured to display a QR code (or "matrix code" elsewhere herein). The QR code may, in some embodiments, be used as a patient's private key and may, when scanned from the display of the first electronic device, cause the present invention to unlock, decrypt, or otherwise permit access to one or more items of user-specific data.

Figure 2:
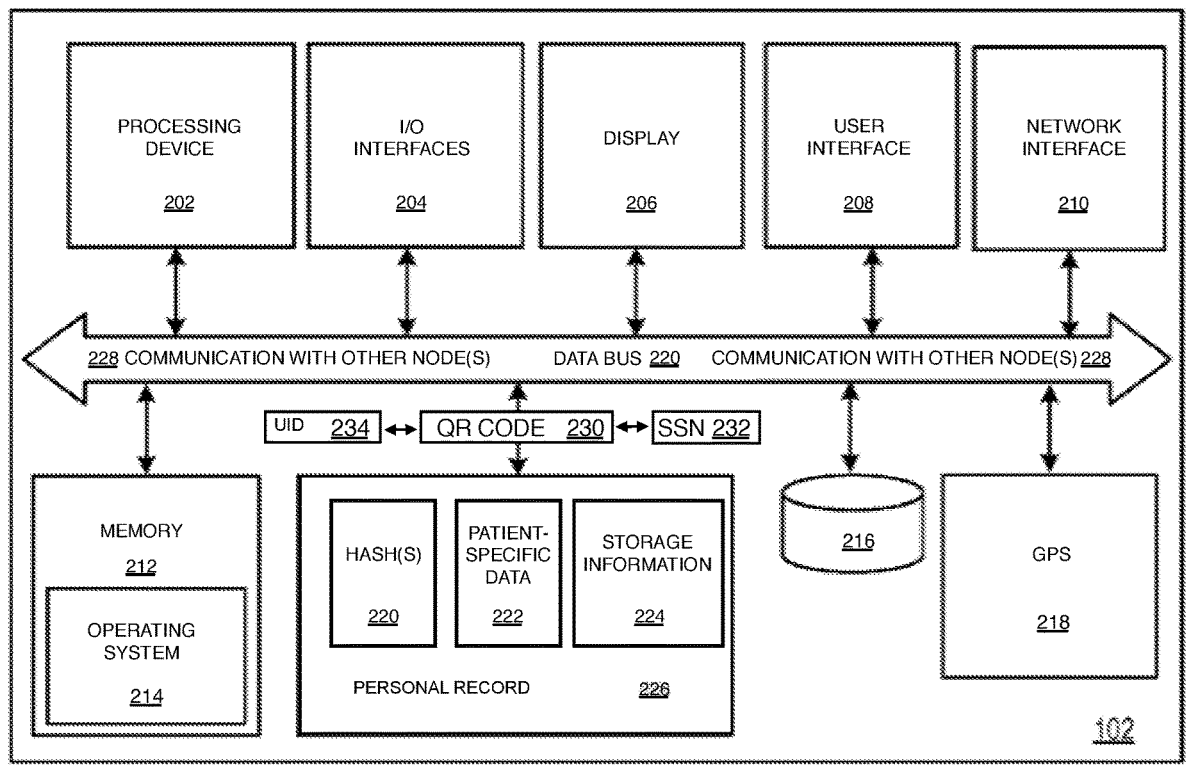
FIG. 2 illustrates an exemplary embodiment of a mobile device shown in FIG. 1.

FIG. 2 illustrates at least one node 201, wherein each node 201 may, in some embodiments, comprise a networked computer system within personal record chain-configured database 108. In some embodiments, mobile devices 102, 104, and 106, and desktop computer 103 may, in addition to their roles as either a first electronic device or a second electronic device, may alternatively or simultaneously comprise at least one node 201.

In the embodiment depicted in FIG. 2, node 201 may comprise, at least, at least one processing device (processor) 202, at least one input/output interface 204, at least one display 206, at least one user interface 208, at least one network interface 210, at least one memory 212, at least one operating system 214, at least one mass storage 216 and at least one GPS 218, with each communicating across a local data bus 232. Additionally, at least one node 201 may create and store at least one personal record (PR) 226, in this exemplary case a patient's record, that may comprise, at least, one or more hash(s) 220, one or more items of user-specific data 222, and at least one element of storage information 224. In some embodiments, node 201 may communicate with other node(s) 228 via one or more networks (not shown in FIG. 2). Additionally, an individual QR code 230 may act as a private key that may enable one or more nodes 201 to access user-specific data 222 in an unencrypted or deidentified, or both, form.

FIG. 2 also discloses additional roles of QR code 230. In some embodiments, a user may select, using sequences described elsewhere herein, whether QR code 230 will act as the key for PR 226, social security number (SSN) 232, or Universal ID (UID) 234. As noted in FIG. 2, these operations are contemplated to be distinct function such that if QR code 230 is accessed in relationship to SSN 232, for example, the user is not inadvertently also decrypting or displaying PR 226 or UID 234. In some embodiments, the security of QR code 230 itself together with the fact that the decryption sequences of QR code 230 and PR 226, SSN 232, and UID 234 are separate, reflects one of many sources of data security in the present invention. Additionally, in some embodiments and as described above, QR code 230 may itself be or substitute for an individual's SSN 230.

As the present invention contemplated a distributed personal record chain computer system wherein each node 201 may communicate with one or more nodes 102, and in some embodiments all other nodes 102, one or more elements of node 201 may be absent in any particular node 201 or shared across one or more nodes 102. In some embodiments, while it is contemplated that, generally although not required in every case, each node 201 may store a copy of all PR 226 chains across the entire present invention, thereby creating a network of nearly-unhackable computing systems and complete redundancy, one or more other elements may be partially stored on one or more nodes 102, or stored on one node 201 but accessed by another node 201. By way of illustration and not limitation, memory 212 and/or operating system 214 may be partially stored across several nodes 102 but accessed by multiple nodes 102, or may be stored on one or more nodes 102 and accessed by nodes 102 that do not have their own memory 212 and/or operating system 214.

The processing device 202 may include any custom made or commercially available processor, a central processing unit (CPU) or an auxiliary processor among several processors associated with node 201, a semiconductor based microprocessor (in the form of a microchip), a macroprocessor, one or more application specific integrated circuits (ASICs), a plurality of suitably configured digital logic gates, and other electrical configurations comprising discrete elements both individually and in various combinations to coordinate the overall operation of the system.

The memory 212 can include any one of a combination of volatile memory elements (e.g., random-access memory (RAM, such as DRAM, and SRAM, etc.)) and nonvolatile memory elements. The memory typically comprises native operating system 214, one or more native applications, emulation systems, or emulated applications for any of a variety of operating systems and/or emulated hardware platforms, emulated operating systems, etc. For example, the applications may include application specific software which may comprise some or all the components of node 201. In accordance with such embodiments, the components are stored in memory and executed by the processing device. Note that although depicted separately in FIG. 2, the system, method, and apparatus for universally accessible personal records 100 may be resident in memory such as memory 212. As mentioned above, in some embodiments, one or more nodes 102 may not have their own memory 212 and/or operating system 214 or may store incomplete memory 212 and/or operating system 214, and may therefore draw upon other nodes 102 for use of one or more memory units 212 and/or operating system elements 214 via node 201 to node 201 communication 228, as discussed herein.

User interface 208 may be configured to detect contact within the display area of the display 206 and may provide such functionality as on-screen buttons, menus, keyboards, etc. that allows users to navigate user interfaces by touch. User interface 208 may also be a keyboard, a mouse, a microphone, a vision tracking system, a motion-capture system, a trackball, or any other known interface with a computing system. For some embodiments, node 201 may also comprise GPS 218 or other means to determine the location of the node 201.

One of ordinary skill in the art will appreciate that the operating system 214 can, and typically will, comprise other components which have been omitted for purposes of brevity. Note that in the context of this disclosure, a non-transitory computer-readable medium stores one or more programs for use by or in connection with an instruction execution system, apparatus, or device. With further reference to FIG. 2, network interface device 210 comprises various components used to transmit and/or receive data over a networked environment such as depicted in FIG. 1. When such components are embodied as an application, the one or more components may be stored on a non-transitory computer-readable medium and executed by the processing device.

As discussed elsewhere in the present disclosure, user-specific data 222 may be viewed by a user, the node 201, or other nodes 102 in several forms, among them an unencrypted form, an encrypted but readable form having patient-identifying information, an encrypted but readable form displaying deidentified user-specific data, encrypted and unintelligible user-specific data 222, or any other form or copy of user-specific data 222. By way of illustration and not limitation, in some embodiments, an unencrypted copy of user-specific data 222 may be available to a user who has accessed the patient's QR code 230 or other private key interface. When existing on the present invention's personal record chain database 108, user-specific data 222 may exist in any form discussed herein or known in the art, including any level of encryption or deidentification, or no encryption or deidentification.

In some embodiments, user-specific data 222 may be stored in one language, generally the patient's native language. In some embodiments, however, the present invention may provide, through memory 212 or any other element of the present invention including elements known to the art but not disclosed in FIG. 2, that the user-specific data 222 may be translated into a selected language by the end user, such as by way of illustration and not limitation, a healthcare provider. For example, the present invention may provide that user-specific data 222 may be stored in English, but when accessed by a user, by using one or more of mobile device(s) 102, 104, 106 or desktop computer 103 to access user-specific data 222 via QR code 230, the user-specific data 222 may be translated into the language of the accessing device, here mobile device(s) 102, 104, 106 or desktop computer 103. This change may be automated in some embodiments, and may save users such as healthcare professionals valuable time.

Storage information 224, as discussed in more detail herein, are generally contemplated to comprise a mathematical problem to be solved. Once a node 201 has reached the solution, the next block may be linked or "chained" to the present PR 226, creating the "personal record chain" known in the art. Such chaining may comprise, in some embodiments, recording the hash of a first PR 226 in or on a second PR 226. In some embodiments, therefore, the chain may be traced by examining the corresponding hashes of each PR 226 to make sure that they match as intended.

Continuing with FIG. 2, the genesis PR 226 may provide for only one hash(s) 220 that may comprise a timestamp (at least) hash of its creation. For all other PRs 226, hash(s) 220 may comprise a timestamp (at least) hash 220 of the creation of the present PR 226 as well as the hash 220 of the previous PR 226.

As discussed elsewhere herein, each PR 226 may comprise, at least, one or more hash(s) 220, one or more items of user-specific data 222, and one or more storage information 224. In some embodiments, an identical copy of each PR 226 may be stored on one or more nodes 201. In some embodiments, an identical copy of each PR 226 may be stored on each node 201.

Remaining with FIG. 2, the present invention may be, and is contemplated generally to be, configured such that one or more nodes 201 may communicate with each other 228. The node 201 to node 201 communication system 228 provides for and enables one or more redundancy and/or data security protections of the present invention. Using node 201 to node 201 communication system 228, one or more nodes 201 of the present invention may all update one or more PRs 226 and PR 226 chains, hashes 220, copies of user-specific data 222, and any other element that the present invention may store on a node 201. One or more nodes 201 may utilize node 201 to node 201 communication system 228 to share one or more storage information 224, thereby enabling one or more nodes to chain a new PR 226 to a previous PR 226. Additionally, one or more nodes 201 may utilize node 201 to node 201 communication system 228 to share one or more node 201 elements, such as but not limited to, part or all of a node's 201 at least one processing device (processor) 202, at least one input/output interface 204, at least one display 206, at least one user interface 208, at least one network interface 210, at least one memory 212, at least one operating system 214, at least one mass storage 216, at least one GPS 218, and/or at least one local data bus 232.

In some embodiments, a QR code 230 may be used by the present invention as a private key. In some embodiments, when a healthcare provider scans a patient's QR code 230, such as by way of illustration by using one or more of mobile devices 102, 104, 106 and/or desktop computer 103, the present invention may provide one or more items of user-specific data 222 to the healthcare professional in an unencrypted form, or a form having a mixture of encrypted and intelligible user-specific data 222. In some embodiments, the health care provider may access the full PR 226 and a fully unencrypted or fully intelligible record of the user-specific data 222. In some embodiments, only one QR code 230 may be used at a time, and in some embodiments, only by the authorized user of mobile device(s) 102, 104, 106 or desktop computer 103 who initiated access via the QR code 230 in the first place. In some embodiments, the patient's QR code 230 may be used by more than one mobile device 102, 104, 106 or desktop computer 103 at a time. It is contemplated that the patient may be able to set preferences within the present invention, or utilize a secondary document such as a wallet card, to determine who or what may utilize the patient's QR code 230, in what manner, and to what extent.

The present invention may provide that when a QR code 230 is utilized to access a patient's PR 226, the present invention initiate storage information 224 to create a new hash 220 within a new PR 226 that links to the accessed PR 226, in the manner known in the block chain database art and generally described herein. By creating a linked series of chained PRs 226, it is contemplated that the present invention may provide a secure chain of medical history information.

In FIG. 2, data is shown progressing both directions between data bus 232 and PR 226 through QR code 230. In some embodiments, this bidirectional arrow is meant not to connote that the QR code 230 itself transfers data back and forth, but rather that, generally, PR 226 may in some embodiments be stored within node 201 and may communicate with data bus 232. In some embodiments, the role of QR code 230 is one-directional, wherein a user via mobile device(s) 102, 104, 106 or desktop computer 103 may utilize QR code 230 to access PR 226, whereupon data bus 232 or any other element of node 201 may transfer one or more elements of user-specific data 222 from PR 226 to the user's electronic device, such as but not limited to mobile device(s) 102, 104, 106 or desktop computer 103.

In order to facilitate the aforementioned functionality, various aspects may be performed by one or more of desktop computer 103 and/or mobile devices 102, 104, and 106, or any node 201 which may be but is not limited to desktop computer 103 and/or mobile devices 102, 104, and 106. In one embodiment, the desktop 103, mobile devices 102, 104, and 106, and/or any node 201 are operative to perform, at least in part, the method depicted in the flowchart of FIG. 3 and described above.

Figure 3:
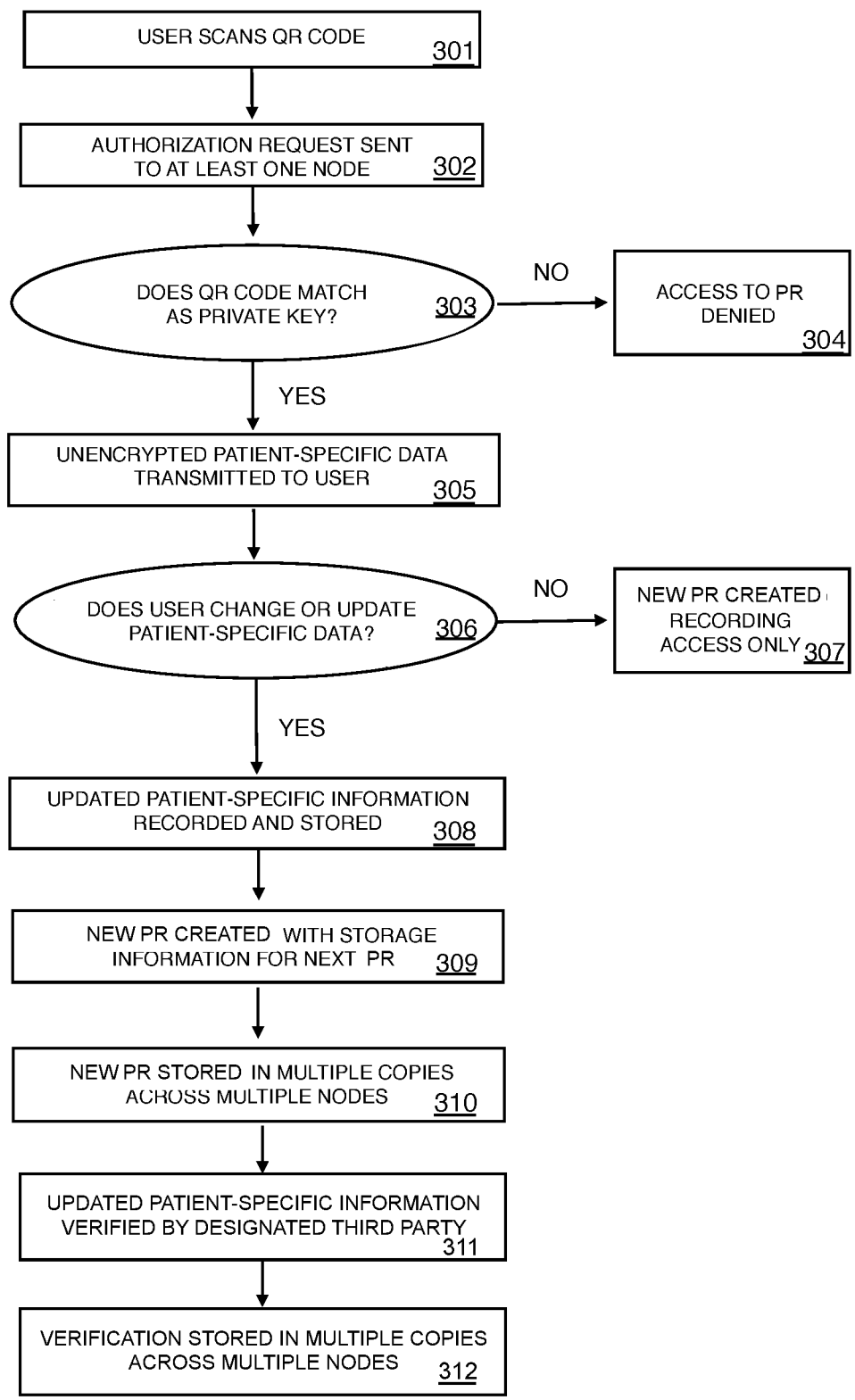
FIG. 3 is a flowchart depicting an exemplary embodiment of a system for universally accessible personal records.

Turning attention to FIG. 3, an exemplary system for universally accessible personal records is disclosed. First, a user may scan a QR code 301 that has been keyed to an individual's PR 226 as disclosed elsewhere herein. Next, the present invention may generate an authorization request and may send the authorization request to at least one node 302. The at least one node may evaluate whether the QR code associated with the authorization request matches the PR 226 as the PR's 226 private key 303.

If the authorization request and the QR code associated with the authorization request do not match with the PR 226, the present invention may deny access 304 to the PR 226. If the authorization request does match with the PR 226 in question, the present invention may transmit either partially or entirely unencrypted user-specific data to the user 305.

The present invention may then analyze whether the user-specific data is merely viewed, or if it has been changed 306 by the user. If the user-specific data was only viewed, or if the only change was that the user-specific data was viewed, the present invention may create a new PR 226 recording that the user-specific data was viewed and not altered 307, and may do so via at least one sequence described elsewhere herein. In some embodiments, the patient or authorized user may control if and when a new PR 226 is created recording the view-only action. The PR 226 recording access-only may include chaining instructions for the next PR 226.

If, however, the user does change or alter one or more item of user-specific data 308 in the PR 226, the present invention may update and store the new user-specific data 308, in some embodiments, as an updated complete record of the user-specific data 308. The present invention may also create a new PR 226, wherein the PR 226 records updated user-specific data 309, and in some embodiments, also records the fact that a change was made to the user-specific data the changes to the user-specific data. In some embodiments, the patient or authorized user may control if and when a new PR 226 is created recording the viewing and changes to user-specific data 308. The PR 226 containing the updated user-specific data and the fact of the changes may include chaining instructions for the next PR 226.

The present invention may also provide that the new PR 226 of either scenario (the viewed but not changed PR 226 of step 307 or the PR 226 including the updated user-specific data of step 309) may be stored in identical copies across at least one more node 310 as described in more detail elsewhere herein. Additionally, it is contemplated that any updated patient or user-specific information created within the PR may be verified by a designated third party 311, such as a medical professional or physician discussed throughout this exemplary embodiment. In the event that a medical professional or other designated third party creates information or updates to the patient or user-specific information recorded and stored within the system, it is contemplated that the user or patient themselves may verify the updated information. In any event, verification of such patient or user-specific information or data may be stored in multiple copies across multiple nodes 312.

It is contemplated that, in some embodiments, the above-described method may be performed on any node. In other embodiments, one or more nodes may perform the method and share 310 the new PR 226 with nodes not designated to perform the above-described method, but are configured to house, chain, and store one or more PRs 226.

If embodied in software, it should be noted that each block depicted in the accompanying flowcharts represents a module, segment, or portion of code that comprises program instructions stored on a non-transitory computer readable medium to implement the specified logical function(s). In this regard, the program instructions may be embodied in the form of source code that comprises statements written in a programming language or machine code that comprises numerical instructions recognizable by a suitable execution system such as desktop 103, mobile devices 102, 104, and 106, and/or any node 201. The machine code may be converted from the source code, etc. If embodied in hardware, each block may represent a circuit or a number of interconnected circuits to implement the specified logical function(s).

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

CONCLUSIONS, RAMIFICATIONS, AND SCOPE

While certain embodiments of the invention have been illustrated and described, various modifications are contemplated and can be made without departing from the spirit and scope of the invention. Accordingly, it is intended that the invention not be limited, except as by the appended claim(s).

The teachings disclosed herein may be applied to other systems, and may not necessarily be limited to any described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions and concepts of the various references described above to provide yet further embodiments of the invention.

Particular terminology used when describing certain features or aspects of the invention should not be taken to imply that the terminology is being refined herein to be restricted to any specific characteristics, features, or aspects of the present invention with which that terminology is associated. In general, the terms used in the following claims should not be constructed to limit the present invention to the specific embodiments disclosed in the specification unless the above description section explicitly define such terms. Accordingly, the actual scope encompasses not only the disclosed embodiments, but also all equivalent ways of practicing or implementing the disclosed present invention. The above description of embodiments of the present invention is not intended to be exhaustive or limited to the precise form disclosed above or to a particular field of usage.

While specific embodiments of, and examples for, the present invention are described above for illustrative purposes, various equivalent modifications are possible for which those skilled in the relevant art will recognize.

While certain aspects of the present invention are presented below in particular claim forms, various aspects of the present invention are contemplated in any number of claim forms. Thus, the inventor reserves the right to add additional claims after filing the application to pursue such additional claim forms for other aspects of the present invention.

What is claimed is:

1. A system for storing, receiving, and authenticating, universally accessible records, comprising:
   a decentralized electronic database distributed across a plurality of nodes, each of the plurality of nodes operative to securely verify, store, update, link, encrypt, and transmit a user's personal records, which comprise a plurality of the user's medical history, charts, laboratory or imaging tests, healthcare provider notes and diagnosis, patient notes, educational records, financial records, ancestral data, journal entries, and letters as a combination of private and publicly created bibliographic records and longitudinal medical records, in a personal record chain, wherein the user's personal records comprise one or more immutable hashes, one or more items of user-specific data, and at least one element of storage information;
   at least one electronic computing device of the user associated with a universal ID unique to the user, corresponding to the user's personal records, and assigned to the user at birth, immutably spanning the entire life of the user, wherein the universal ID is additionally printed on a card comprising a quick response (QR) code, and the universal ID is a key operative to decrypt the user's personal records;
   at least one other electronic device, operative to
      scan the QR code;
      access at least some of the user's personal records;
      generate and transmit an update to the accessed user's personal records while avoiding overriding, deleting, or permanently altering earlier versions of the accessed user's personal records, wherein the update is a new hash successively chained to the one or more hashes in the user's personal records to update the user's personal record chain distributed across each of the plurality of nodes; and
      translate the decrypted user's personal records into a language specified at a time of the access;
   wherein the update is supplied by the user and is further verified by a third party designated according to a type of personal information defining the update; and wherein verification of the update is immutably recorded in the personal record chain, in support of personal record accuracy and continuity of care, and wherein, the user's personal records remain under the ownership, control, and possession of the user associated with the universal ID.

2. The system of claim 1, wherein the at least one electronic computing device of the user comprises a mobile electronic device or a desktop computer of the user.

3. A method for storing, receiving, and authenticating universally accessible records, comprising the steps of:

providing
- a) a decentralized electronic database distributed across a plurality of nodes,
- b) a universal ID unique to a user, corresponding to the user's personal records and assigned to the user at birth, immutably spanning the entire life of the user, the universal ID printed on a card and additionally stored as a quick response (QR) code,
- c) a mobile device of the user, and
- d) at least one electronic device;

receiving, at the mobile device of the user, the user's personal records, wherein the user's personal records comprise a plurality of the user's medical history, charts, laboratory or imaging tests, healthcare provider notes and diagnosis, patient notes, educational records, financial records, ancestral data, journal entries, and letters, as a combination of private and publicly created bibliographic records and longitudinal medical records;

verifying, storing, updating, linking, encrypting, and transmitting, at each of the plurality of nodes, the user's personal records in a personal record chain;

scanning, at the at least one electronic device, the QR code, wherein the QR code is a private key operative to permit access to the user's personal records;

decrypting, at the universal ID, the user's personal records;

accessing, at the at least one electronic device, the user's personal records;

generating, at the mobile device of the user or the at least one electronic device, an update to the user's personal records, wherein the update records access to the user's personal records;

receiving, at the plurality of nodes, the update to the user's personal records; and verifying, storing, updating, linking, encrypting, and transmitting, at each of the plurality of nodes, the update to the user's personal records, wherein, the user's personal records remain under the ownership, control, and possession of the user assigned the universal ID.

4. The system of claim 1, wherein the at least one other electronic device comprises a mobile electronic device or a desktop computer of the user.

5. The method of claim 3, wherein the update further comprise recording an alteration to any of the user's personal records.

* * * * *